United States Patent [19]

Verbeek et al.

[11] 4,049,689

[45] Sept. 20, 1977

[54] METHOD FOR THE PREPARATION OF ALKYL TIN HALIDES

[75] Inventors: François Verbeek, Harmelen; Eric J. Bulten, Bilthoven; Jan W. G. van den Hurk, Leusden, all of Netherlands

[73] Assignee: Commer S.r.l., Lodi (Mi), Italy

[21] Appl. No.: 634,255

[22] Filed: Nov. 21, 1975

[30] Foreign Application Priority Data

Nov. 22, 1974 Netherlands .................. 7415247

[51] Int. Cl.$^2$ .............................................. C07F 7/22
[52] U.S. Cl. ............................. 260/429.7; 204/158 R
[58] Field of Search ................. 260/429.7; 204/158 R

[56] References Cited

U.S. PATENT DOCUMENTS

| 3,387,011 | 6/1968 | Coates et al. | 260/429.7 |
| 3,397,131 | 8/1968 | Kircher et al. | 204/158 R |
| 3,404,167 | 10/1968 | Gray et al. | 260/429.7 |
| 3,414,595 | 12/1968 | Oakes | 260/429.7 |
| 3,449,451 | 6/1969 | Senatore | 260/429.7 X |
| 3,475,472 | 10/1969 | Suzuki et al. | 260/429.7 |
| 3,745,183 | 7/1973 | Katsumura et al. | 260/429.7 |

OTHER PUBLICATIONS

Miretskii et al., Chem. Abstr. 69,77397s (1968).
Abramova et al., Chem. Abst. 58,1139c (1963).
Vereshchinskii et al., Chem. Abst. 65,8962f (1966).
Fentiman et al., J. Organometal. Chem. V4,302-7 (1965).
Fentiman et al., J. Organometal. Chem. V6, 645-651 (1966).
Sisido et al., J. Organometal. Chem., V9,109-115 (1967).
Sawyer Organotin Cpds., Marcel Dekker, Inc. N.Y. V1, p. 21 (1971).

*Primary Examiner*—Helen M. S. Sneed
*Attorney, Agent, or Firm*—Spencer & Kaye

[57] ABSTRACT

In the process for the preparation of alkyl tin halides by means of direct conversion of tin with aliphatic halides, the alkyl halide is fed in such a way gradually to the gas space over the further reaction components that there is an overpressure of no more than a few cms of mercury. The reaction is carried out in the presence of a liquid acid amide in quantities of 0.65 to 2.3 mol per gramatom of tin and in the presence of catalytic amounts of iodine and/or iodide at raised temperatures. The reaction is promoted under the influence of ultraviolet irradiation and by the addition of a catalyst of the type promoting free radial initiation reactions.

11 Claims, No Drawings

METHOD FOR THE PREPARATION OF ALKYL TIN HALIDES su

BACKGROUND OF THE INVENTION

The invention relates to the preparation of alkyl tin halides by means of direct conversion of tin with aliphatic halides under the influence of liquid compounds of the acid amide type and of iodine and/or iodide as a catalyst.

Such reactions are known in the art under application of a phosphorus compound with at least one nitrogen atom in the molecule as a catalyst. It has also been suggested to use organic nitrogen compounds and ammonium halides as catalysts.

The reaction is mostly carried out at temperatures between 130° C and 230° C.

Because the boiling points of the lower alkyl halides are below 150° C, the preparation of the lower alkyl compounds so far has been carried out under raised pressure in a pressure vessel.

In so far as sporadically was operated at atmospheric pressure, it was found to be difficult to control the gas supply such that the alkyl halide supplied was just consumed, so that only a low rate of conversion was attained.

SUMMARY OF THE INVENTION

It is the object of the invention to provide a method of preparation that also can be carried out for the lower aklyl compounds at atmospheric pressures at high yields.

The invention comprises that the aliphatic alkyl halide is fed in such a way gradually to the gas space over the further reaction components that there is no more than a few cm mercury overpressure and that the liquid acid amide component is present in quantities of 0.65 - 2.3 mol per gramatom tin.

DETAILED DESCRIPTION OF THE INVENTION

The highly polar reaction medium is very promotive for the reaction. Addition of further solvents is superfluous and was even found to be adverse where it concerns compounds that reduce the polarity of the reaction medium, such as apolar hydrocarbons.

The alkyl compounds that have a boiling-point below that of the reaction temperature can be fed in a gaseous condition into the reaction vessel.

It appears that the reaction mostly proceeds so well that in a case of too slow a feeding an under-pressure is caused, so that it is advisable to seal the reaction room from the environment by means of a mercury seal.

The reaction can be carried out with alkyl iodides and alkyl bromides, but preferably with alkyl chlorides. In general the chlorides are cheaper raw materials and in the present method the lower boiling-point does not cause any difficulties.

The reaction proceeds in the most simple way in case of methyl chloride, which is also gaseous at ambient temperature. The liquid alkyl halides can be fed via a tube that is kept at reaction temperature, so that too great a local cooling down of the reaction mixture is avoided.

The halide, however, may also be fed into the reaction room via a room separately brought at the reaction temperature. Also in case of the higher boiling alkyl halides it is advantageous to feed them gradually to the reaction liquid and to prevent by means of a mercury seal or the like the entry of oxygen into the reaction room.

The tin can be applied in the form of a thin foil or as tin sponge, or also as a finely divided powder with particle diameters between 0.05 and 0.3 mm.

The reaction is mostly carried out at temperatures between 130° C and 160° C.

Furthermore, it has been found that the reaction can be carried out at temperatures below 130° C and even between 65° C and 100° C with reasonable yields if a radical initiation is promoted.

For this purpose a catalyst of the free radical initiator type can be added, e.g. in quantities of 0.02 to 1.0 mol percent. A suitable catalyst, for instance, is azo-bis-isobutyronitrile. One and the same effect can be obtained if by way of radical initiation the reaction mixture is irradiated with U.V. light.

Organic acid amides that may be used are i.a. acetamide, dimethylformamide, methylformamide, substituted or non-substituted propionic acid amides and substituted or non-substituted phosphoric acid amides and phosphorous acid amides, such as hexamethyl phosphoric acid triamide, hexa-ethyl phosphoric acid triamide and hexabutyl phosphoric acid triamide, hexamethyl phosphorous acid triamide and related liquid polar amide compounds.

DESCRIPTION OF THE PREFERRED EMBODIMENTS

EXAMPLE I

Into a reaction vessel provided with a reflux condenser and stirrer, was brought a mixture of 19.9 gs. (0.116 grat) of tin powder (diameter 0.05 - 0.3 mm)

30 mls. (0.164 mol) of hexamethyl phosphoric triamide (HMPT)

4.5 gs. of sodium iodide (0.03 mol)

Via a gas inlet tube the air in the reaction vessel was replaced by an atmosphere of methylchloride gas, a constant methylchloride pressure of approximately 3 cm pressure being maintained with the acid of a mercury seal connected with the discharge opening of the cooler.

As a result of the heat of solubility of methyl chloride in the reaction mixture the temperature rose to 40° C. While being stirred vigorously, the mixture was heated at 140° C - 150° C, methylchloride being taken up quickly. After approximately 40 minutes the tin powder had been converted completely. After a total reaction time of 3 hours at 140° C - 150° C the reaction mixture, solid at ambient temperature, was taken up in 200 mls. of methanol and analyzed with the aid of a Nuclear Magnetic Resonance (NMR), a weighed out quantity of tetramethyl germanium ($Me_4Ge$) being used as internal standard.

From the results of the analysis it was found that of the initial amount of tin 94% had been converted into dimethyl tin dichloride and 4% into trimethyl tin chloride, whereas no methyl tin trichloride could be shown.

EXAMPLE II

In the same way as described in example I a test was carried out, in which tin foil was used (of a thickness of 0.009 mm) (instead of tin powder). After 3 hours at 140° C - 150° C the tin had been converted completely, 87% of dimethyl tin chloride and 5% of trimethyl tin chloride being formed.

EXAMPLE III

In the same way as described in example I a test was carried out, in which tin sponge (obtained by casting molten tin into water) was used. After 3 hours at 140° C – 150° C the tin had been converted completely while forming 93.5% of dimethyl tin dichloride and 6% of trimethyl tin chloride.

EXAMPLE IV

In the same way as described in example I a test was carried out with 20 mls. of HMPT (instead of 30 mls.). After 2.5 hours at 140° C – 150° C 83% of tin had been converted. Of the tin converted it was found that 89% had been converted in dimethyl tin dichloride and 6% into trimethyl tin chloride.

EXAMPLE V

In the same way as described in example I a test was carried out, a catalytic quantity of 20 mol percent (6 mls.) of HMPT being used (instead of 30 mls.) After 3 hours at 140° C – 150° C 52% of tin had been converted, while forming 23% of dimethyl tin dichloride and 29% of trimethyl tin chloride (based on the amount of tin converted).

From examples IV and V it appears that unsatisfactory results are obtained, both in terms of tin conversion and product composition, if HMPT is used in catalytic amounts instead of as a solvent. Optimum results are obtained at a molar ratio HMPT $\geq$ 2/3 preferably HMPT/tin 1 to 2.

EXAMPLE VI

In the same way as described in example I a test was carried out, as a polar solvent being used 30 mls. of dimethylacetamide (instead of HMPT). After 3 hours at 140° C – 150° C the tin had been converted completely.

Similar results were obtained when the polar solvents methylacetamide, dimethylformamide and methylformamide were used.

Upon using the apolar solvent xylene not any conversion of tin was observed after 5 hours at 140° C – 150° C.

From these results it follows that the reaction is very highly promoted by the use of highly polar solvents.

EXAMPLE VII

In a way entirely in accordance with example I and with the same molar ratios the reaction was carried out at different temperatures and with different alkyl halides as indicated in table A, test *a* being the same as been been described more in detail in example I.

For tests *h* to *m* inclusive the halide was added dropwisely, while maintaining an overpressure of 0.5 – 1.0 cm mercury on a mercury seal immediately connected with the upper end of the reflux condenser cooled by water, after firstly the air having been expelled from the reaction flask.

Like with the examples previously specified it appeared that the reflux condenser was hardly necessary and only served as an extra safeguard.

With tests *g* and *m* the reaction vessel was irradiated with an U.V. lamp at wave lenths of 250 – 600 nm (make Philips, type Sp 500 W) and test *e* a quantity of 5 mol. percent of azo-bis-iso-butyronitril (AIBN) was suspended in 5 mls. of HMPT, distributed over a period of 3.5 hours added to the reaction mixture.

From this it appears that the conversion of tin is highly promoted by promoting the formation of free radicals and in particular by U.V. irradiation.

TABLE A

| test | halide | temperature °C | time (hours) | converted tin % | remarks |
|---|---|---|---|---|---|
| a | methylchloride | 140 – 150 | 3 | 100 % | (= example I) |
| b | " | 120 – 130 | 3 | 100 % | |
| c | " | 100° | 3,5 | 100 % | |
| d | " | 85° | 3,5 | 60 % | |
| e | " | 85° | 3,5 | 80 % | (add AIBN 5 mol %) |
| f | " | 70° | 3 | 36 % | |
| g | " | 70° | 3 | 97 % | U.V.-irradiation |
| h | butylchloride 32,7 g | 140 – 150 | 3 | 78 % | |
| i | butylbromide 48,5 g | 140 – 150 | 2,5 | 86 % | |
| j | octylchloride 53,2 g | 140 – 150 | 3 | 69 % | |
| k | octylbromide 68,3 g | 140 – 150 | 2 | 90 % | |
| l | butylchloride 16,3 g | 70° | 5 | 6 % | quantities halved |
| m | " | 70° | 5 | 52 % | quantities halved U.V.-irradiation |

We claim:

1. A method for the preparation of alkyl tin halides by heating at raised temperature a reaction mixture of metallic tin and an alkyl halide under the influence of a liquid acid amide compound and of iodine and/or iodide as a catalyst, wherein the alkyl halide is fed in such a way gradually to the gas space over the reaction mixture that the reaction proceeds at substantially atmospheric pressure and no more than a few centimeters mercury overpressure, and the liquid acid amide compound is present in quantities of 0.65 to 2.3 mol per gramatom of tin.

2. A method according to claim 1, wherein the acid amide is added at a ratio of 1–2 mol per gramatom of tin.

3. A method according to claim 2, wherein free-radical initiation is promoted in the reaction mixture.

4. A method according to claim 3, wherein a free-radical initiation-catalyst is added to promote the free-radical initiation.

5. A method according to claim 4, wherein 0.02 – 1.0 mol % of azo-bis-isobutyronitrile is added as the free-radical initiation catalyst.

6. A method according to claim 3, wherein the free-radical-initiation is promoted by irradiation of the reaction mixture with U.V.-light.

7. A method according to claim 6, wherein the U.V.-light is applied in the wave length range of 250–600 nm.

8. A method according to claim 3, wherein the temperature during reaction is between 65° C and 100° C.

9. A method according to claim 11, wherein the temperature during reaction is between 100° C and 160° C.

10. A method according to claim 1, wherein the acid amide is a substituted or non-substituted propionic acid amide, a substituted or non-substituted phosphoric acid amide, or a phosphorous acid amide.

11. A method according to claim 1, wherein the acid amide is acetamide, dimethylformamide, methylformamide, hexamethyl phosphoric acid triamide, hexa-ethyl phosphoric acid triamide, hexabutyl phosphoric acid triamide, or hexamethyl phosphorous acid triamide.

* * * * *